United States Patent [19]

Munk

[11] B 3,999,439
[45] Dec. 28, 1976

[54] HIGH PRESSURE SAMPLE INJECTOR AND INJECTION METHOD

[75] Inventor: Miner N. Munk, Walnut Creek, Calif.

[73] Assignee: Varian Associates, Palo Alto, Calif.

[22] Filed: July 22, 1974

[21] Appl. No.: 490,547

[44] Published under the second Trial Voluntary Protest Program on February 24, 1976 as document No. B 490,547.

[52] U.S. Cl. .................................. 73/422 GC
[51] Int. Cl.² .................................. G01N 1/10
[58] Field of Search ............ 73/422 GC; 210/198 C

[56] References Cited

UNITED STATES PATENTS

| 1,081,768 | 12/1913 | Kitts | 251/230 |
|---|---|---|---|
| 2,757,541 | 8/1956 | Watson | 73/422 GC |
| 3,475,950 | 11/1969 | Ferrin | 73/422 GC |
| 3,583,230 | 6/1971 | Patterson | 73/422 GC |
| 3,621,719 | 11/1971 | Goodman | 73/422 GC |
| 3,777,572 | 12/1973 | Hrdina | 73/61.1 C |

FOREIGN PATENTS OR APPLICATIONS

| 1,318,788 | 1/1963 | France | 73/422 GC |

Primary Examiner—S. Clement Swisher
Attorney, Agent, or Firm—Stanley Z. Cole; Gerald M. Fisher; John J. Morrissey

[57] ABSTRACT

An injection apparatus and method for use in high pressure liquid chromatography. A cylindrical sample holding means containing several sample cells is maintained in a chamber whose pressure is approximately equal to that of the head of the chromatograph separation column. The sample cells are bores through the cylinder, parallel to its axis and spaced along a cylinder of revolution concentric to the axis. The cells are preloaded with samples to be analyzed. Stationary carrier fluid inlet and outlet conduits extend into the chamber above and below corresponding points on the cylinder defined by the sample cell placement. The inlet conduit is connected to a high pressure source of carrier fluid. As the sample holder is rotated, successive sample cells are aligned with the inlet and outlet conduits such that the sample is forced through the outlet conduit into the column. This structure eliminates the need for movable high pressure seals between the outlet conduit and the sample cells, due to the maintenance of all the cells at an elevated pressure.

14 Claims, 6 Drawing Figures

HIGH PRESSURE SAMPLE INJECTOR AND INJECTION METHOD

BACKGROUND OF THE INVENTION

1. Field of the Invention.

This invention relates to method and apparatus for injecting samples of material into a high pressure environment. More particularly, the invention pertains to sample injection apparatus for use in liquid chromatography.

2. Description of the Prior Art.

Liquid chromatography pertains to a particular variety of equipment and techniques for analyzing the components of an unknown sample of liquid material, qualitatively and/or quantitatively. According to chromatographic techniques, a column is provided which is packed with a finely divided material. The packing material provided is chosen in accordance with its affinity for attracting certain elements to adsorb, or cling to it. When the sample is forced through the column, each of the components passes through the column in a time pattern which is a function of the degree of tendency of that component to be adsorbed by the packing material. By detecting variations in properties of the substance emerging from the column, and plotting these variations against time, certain information can be derived as to the nature and amount of the components of the unknown sample. For example, the presence of a given component of the sample may be known to effect a change in a particular property of the liquid emerging from the column such that a maximum value of that property will occur at a predetermined time after the sample is introduced into the column. By observing where such peaks occur, the nature of various components of the sample may be determined with a significant degree of certitude and repeatability.

In liquid chromatography, it is customary to introduce the sample into the column immediately previous to the introduction of another liquid, called a carrier, in order to dissolve the sample and drive it through the column. It has been found that if the sample is driven through the column at very high pressure, a consequent reduction in the time for analysis of each sample is observed, due to the more rapid passage of the sample through the column. One of the problems in high pressure chromatography is the need for stopping the flow of the carrier into the column during the introduction of the sample. This need arises because of the inherent difficulties in injecting a second substance into a stream flowing at high pressure. It is difficult to provide high pressure seals which are durable and reliable and which are capable of accomplishing or allowing this function. Also, the necessity for interrupting carrier flow slows down the operation.

In liquid chromatography, it is often very useful to utilize a mechanism containing several cells or separate containers for samples, into which various samples for analysis can be pre-loaded. After preloading, the cells are successively connected to the column and the pressure elevated to inject the sample into the column. This desirability of simultaneously loading multiple samples, and subsequently successively driving them through the column, necessitates the provision of a large number of movable high pressure seals. Such apparatus is inherently quite expensive and difficult to machine, and the seals involved are often of dubious reliability and limited durability.

SUMMARY OF THE INVENTION

The objects of this invention are accomplished by means of an apparatus including a sample holding means incorporating a number of sample cells for holding samples of material to be analyzed. The sample holding means is generally cylindrical in configuration, the sample cells being circular bores lengthwise through the cylinder parallel to its axis, each having an inlet and outlet port at its opposite ends. The centers of the sample cells are equidistant from the axis of the cylinder. The sample holding cylinder is rotatably positionable within a pressure-tight vessel, optimally on a shaft extending through a wall of the vessel via a high pressure shaft seal. The vessel is connected by means of an outlet conduit to a high pressure liquid chromatographic analysis column. This connection enables the maintenance of the vessel containing the sample holding means at a pressure which is roughly equal to that of the analysis column.

The vessel is also provided with an inlet conduit connected to a source of carrier liquid at pressure sufficient to drive the carrier liquid into the vessel. The inlet conduit and outlet conduit are positioned at opposite ends of the cylindrical sample holding means at corresponding points on the cylinder defined by the centers of the sample cells. The inlet and outlet conduits thus extend each to a point adjacent a respective one of the inlet port and outlet port of whatever sample cell is positioned adjacent the conduits establishing the carrier stream.

This configuration causes successive ones of the sample cells to become aligned simultaneously with the input and outlet conduits of the vessel as the cylindrical sample holding means is rotated. When a sample cell becomes aligned with the inlet and outlet conduits, the pressure of the carrier fluid entering the inlet conduit forces the sample in that cell through the outlet conduit and into the analysis column.

The transfer of the sample from the input conduit through the outlet conduit and into the analysis column takes place in the absence of a high pressure drop along the way. This means that only a low pressure seal need be provided between the outlet and inlet ports of each of the sample cells and the inlet and outlet conduits of the vessel.

Such a seal is provided with tetrafluoroethylene (hereinafter called "Teflon") gaskets which are pressed adjacent the ends of the cylindrical sample holding means. The gaskets are pivoted at the center of the cylindrical sample holding means for rotation relative thereto, and are retained stationary with respect to the vessel.

The gaskets have apertures which are positioned adjacent the inlet and outlet conduits of the vessel and at corresponding points on the circles defined by the centers of the inlet and outlet ports of the sample cells. As the cylinder is rotated with respect to the gaskets, the outlet ports of each of the sample cells become successively aligned with the apertures in the gaskets. Those ports of the sample cells which are not so aligned are closed with a low pressure seal effected by the pressure of the gaskets against the cylinder.

A resilient spring may be provided to bias the upper gasket downwardly to force together the entire structure, including the two gaskets and the cylindrical sample holding means, the lower gasket (adjacent the outlet ports) being fixedly supported by pins.

The structure described above provides a means whereby a plurality of samples may be preloaded into the several sample cells, and then be successively driven into the analysis column by the selective connection of each sample cell into the stream of carrier fluid under high pressure. The transfer of carrier fluid and sample liquid from the sample cells into the analysis column is accomplished without any need for high pressure seals, there being no substantial pressure drop between the inlet conduit and the column. Therefore, inexpensive and reliable low pressure seals may be employed in this apparatus. With the exception of the shaft seal, the high pressure drop interfaces of the apparatus are not borne by the moving parts thereof. The rotary shaft seal is isolated from the sample compartments and thereby the chance of leakage of sample through this single high-pressure moving seal is eliminated.

Apparatus, such as a ratchet, may suitably be provided and attached to the shaft connected to the sample holding cylinder in order that rotation of the sample holding means may be accomplished in a succession of predetermined increments.

This device has few moving parts and, with the exception of the seal through which the shaft passes, no high pressure interface occurs in the vicinity of any moving part. This enables the utilization of more compact and less expensive moving parts, and increases durability and reliability of the apparatus.

In order to prevent undesirable buildup of static pressure in the line of high pressure carrier fluid entering through the inlet conduit, a particular type of "make before break" valving is employed between the inlet and outlet conduits and the inlet and outlet ports of the respective sample cells. The apertures through the two gaskets are constructed such that the size of the apertures adjacent the inlet and outlet ports is larger than the minimum spacing between adjacent inlet and outlet ports. This means that the apertures can overlap between adjacent inlet or outlet ports, and that the aperture will communicate with the succeeding port before its communication with the previously aligned port ceases. This arrangement provides for a gradual variation in the pressure applied to each port, and assures that the inlet for the carrier fluid is not entirely blocked at any time.

The sample cells in a particular cylinder need not be the same size or volume. Such sample cells may be varied in volume to accommodate varying test purposes, such as might arise if it were desired to inject a rapid succession of varying amounts of the same unknown substance into the analysis column. The sample cells, where desirable, may also contain packing material.

It is sometimes useful to provide the vessel with additional inlet and outlet conduits which are connectable to the sample cells for preloading each of the sample cells with samples without dissembling the apparatus.

It is therefore a major purpose of this invention to provide an apparatus and method for injecting samples of unknown material into a high pressure chromatographic column without halting the flow of carrier liquid used to drive the samples through the column.

It is another important purpose of this invention to provide method and apparatus in liquid chromatography for enabling the preloading of a plurality of samples into a corresponding plurality of sample cells for subsequent rapid introduction to the chromatographic column, and yet alleviate the need for high pressure movable seals between the sample cells and the column.

It is a further object to provide an apparatus and method for introduction of sample materials to a high pressure liquid chromatographic column, without the need for any high pressure seals at all between the sample cells and the column.

It is a consequent object of this invention to provide for high pressure injection of samples in liquid chromatography while transferring the high pressure drop interfaces between the apparatus and the ambient atmosphere to static load bearing elements, rather than imposing these high pressure drops on movable components.

Prior art high pressure injectors are commonly bulky, difficult to make and complex. It is a further object to provide equivalent or superior apparatus which is simple, with few moving parts, less costly and easily machined.

Repeatability of results of the prior art devices is limited by the fact that volume of the sample cells is not uniform. This is due to slight extrusion of components of the high pressure seals into the cell volumes. The absence of the high pressure movable seals near the sample cells of the apparatus eliminates this problem and such elimination is another purpose of this invention.

Prior art multiple sample injectors are, because of their complexity, difficult to automate. An object of this invention is to render automation easy.

A further object of this invention is to provide apparatus and method for injection of quantities of fluid into a high pressure environment with increased facility.

DESCRIPTION OF THE PREFERRED EMBODIMENT

Figure 1:
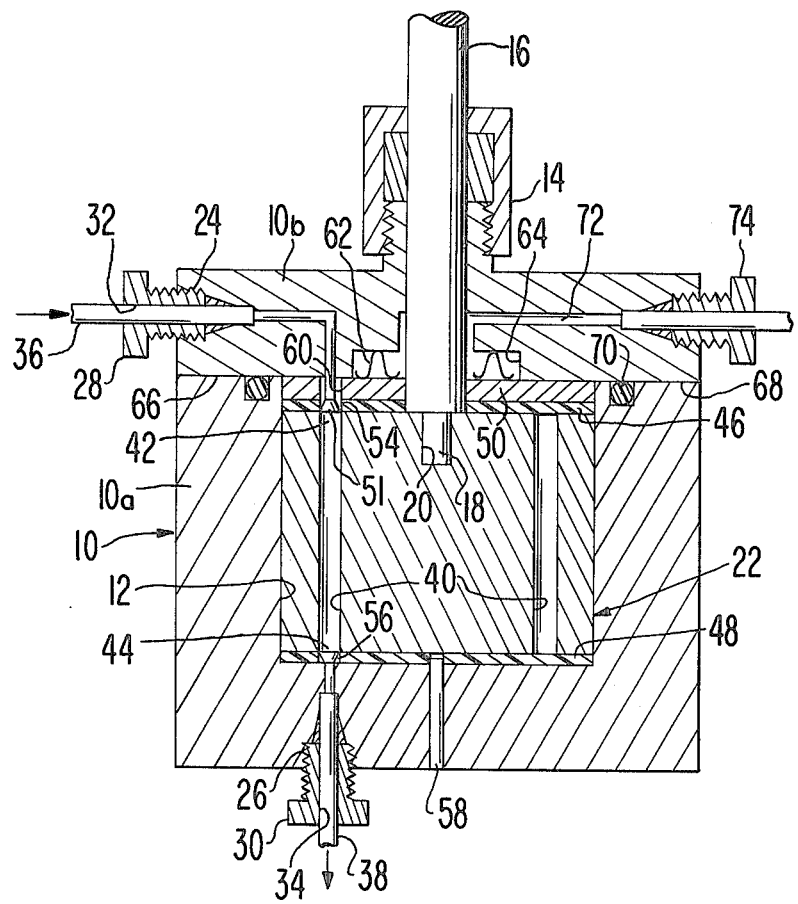
FIG. 1 is a side sectional view of the injector apparatus of this invention.

FIG. 1 shows a vessel 10 which is a closed container and capable of withstanding a high pressure drop between its exterior and the chamber 12 defined therein. Vessel 10 is made up of two separate portions 10a and 10b. These portions meet at interfaces 66 and 68, and are additionally sealed together by an O-ring 70. At the top of the vessel 10 is a high pressure shaft seal 14 through which extends a rotatably mounted shaft 16. Shaft 16 has a protrusion 18 on its lower end which is suitable for engagement in the slot 20 of a cylindrical sample holding means 22. Accordingly, rotation imparted to shaft 16 also rotates the cylindrical sample holding means 22 in a corresponding fashion.

The vessel 10 also has two holes 24 and 26 into which are threadedly fitted plugs 28 and 30. Each of the plugs 28 and 30 has a hollow bore 32 and 34, respectively, through the center thereof. An inlet conduit 36 extends through bore 32 and an outlet conduit 38 extends through bore 34. Inlet conduit 36 is connected to a high pressure source of carrier fluid suitable for use in propelling a sample liquid to an analysis column of a liquid chromatograph. Outlet conduit 38 is connected to the input of a high pressure liquid chromatographic analysis column. This connection maintains the pressure in the chamber at about the same level as the column. The particular structure of the source of carrier fluid and the analysis column are not part of this invention and hence are not shown.

Figure 2:
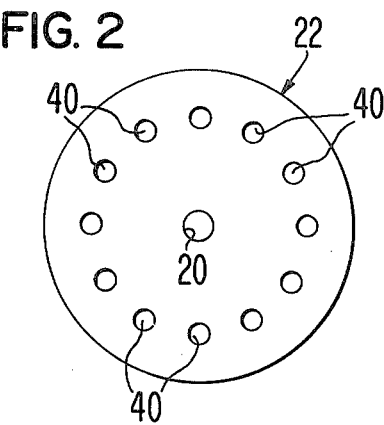
FIG. 2 is a top view of the cylindrical sample holding means of this invention, illustrating the placement of the individual sample cells therein.
Figure 3:
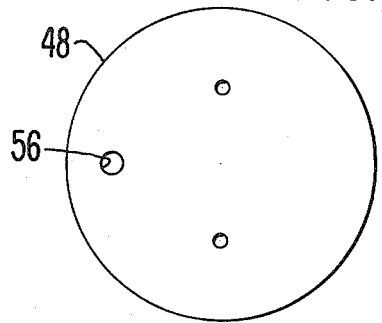
FIG. 3 is a top view of one of the gaskets employed adjacent the ends of the sample holding means of this invention.

A plurality of sample cells 40 are incorporated into the cylindrical sample holding means 22. Each of the sample cells 40 is a circular bore extending entirely through the cylinder 22 from top to bottom and parallel to its axis. Each of the sample cells 40 has an inlet port 42 extending through the top surface of cylinder 22 and an outlet port 44 extending through the bottom surface thereof. As shown in FIG. 2, the plurality of sample cells 40 are disposed with their centers lying along an imaginary cylinder of revolution concentric to the axis of cylinder 22.

Gaskets 46 and 48 are superimposed adjacent the top and bottom surfaces of the cylinder 22, respectively. Each of the gaskets 46 and 48 has an aperture 54 and 56, respectively. The apertures 54 and 56 are positioned directly above and below one another at a distance from the axis of the cylinder 22 which is equal to the radius of the cylinder described by the placement of the sample cells 40 about the axis of the cylinder 22. The inlet conduit 36 communicates with the aperture 54, while the outlet conduit 38 communicates with the aperture 56.

Each of the gaskets 46 and 48 is pivotally mounted concentrically on the cylinder 22 for relative rotation to the cylinder. The gasket 48 is held rotationally stable with respect to the vessel 10 by means of pins 58. This assures that the outlet conduit 38 and the aperture 56 in gasket 48 remain in continuous alignment.

A pressure plate 50 is positioned atop the gasket 46 and has an aperture 60 which is aligned with aperture 54 in the gasket 46, and through which passes a portion of the inlet conduit 36. Gasket 46 and pressure plate 50 are prevented from moving by the presence of a lip 51 which protrudes from the inlet conduit 36 into chamber 12. The lip 51 also reduces diffusion of the incoming carrier fluid as it enters the top of the injector. A flat spring 62 is located in recess 64 in the upper wall 10b of vessel 10. The flat spring 62 resiliently biases the entire assembly including the pressure plate 50, gaskets 46 and 48, and the cylinder 22 downwardly against the pins 58. This biasing of these elements together, and the consequent pressure of gaskets 46 and 48 against the inlet and outlet ports of the sample cells 40 which are not aligned with either of apertures 42 and 44 causes the establishment of a low pressure seal of these covered inlet and outlet ports.

The upper portion 10b of vessel 10 has an orifice 72 to which is connected a bleeder valve 74 to be used in order to limit the pressure of the chamber 12.

The operation of the apparatus described above is as follows. The sample cells 40 of cylindrical sample holding means 22 are filled with the desired amounts of various samples containing unknown components. Specific apparatus and methods for doing this are discussed below. Outlet conduit 38 is connected to the inlet of an analysis column. Inlet conduit 36 is connected to the outlet of a high pressure pump supplying carrier fluid. Shaft 16 is rotated to a degree necessary to position a first one of the sample cells 40 with its inlet port 42 aligned with aperture 54 of the gasket 46, and with its outlet port 44 simultaneously aligned with aperture 56 of the gasket 48. This alignment results in the establishment of a continuous path from inlet conduit 36 to outlet conduit 38.

The pressure of the carrier fluid entering through inlet conduit 36 is maintained at a level somewhat higher than that of the analysis column, but not at a pressure which greatly exceeds the pressure of the analysis column. When the first one of the cells 40 has its inlet and outlet ports aligned with the conduits 36 and 38, respectively, the pressure of the carrier fluid forces the sample from the first sample cell 40 onward into the analysis column, where analysis may be performed by the rest of the liquid chromatograph system in a known fashion.

When the sample has been expelled from the first sample cell 40, shaft 16 may then be rotated far enough to position an adjacent one of the sample cells 40 in alignment with conduits 36 and 38. The carrier fluid pressure then operates to force the sample in the next adjacent sample cell 40 through exit conduit 38, to the analysis column.

When the cylinder 22 is rotated by means of shaft 16, only the cylinder itself rotates, the gaskets 46 and 48 remaining stationary. The top and bottom surfaces of the cylinder 22 slip on the stationary gaskets 46 and 48, respectively. This, as noted above, results in the continuous alignment of apertures 54 and 56 of the gaskets 46 and 48, respectively in the stream of carrier fluid.

It is not necessary to interrupt the flow of carrier fluid through inlet conduit 36 during the rotation of the cylinder 22 in the course of aligning succeeding ones of the sample cells 40 with the stream of carrier fluid. The pressure of the carrier fluid may be maintained, and the samples in succeeding ones of the test sample cells 40 are expelled into the analysis column automatically as each sample cell passes into the carrier flow path.

Figure 4:
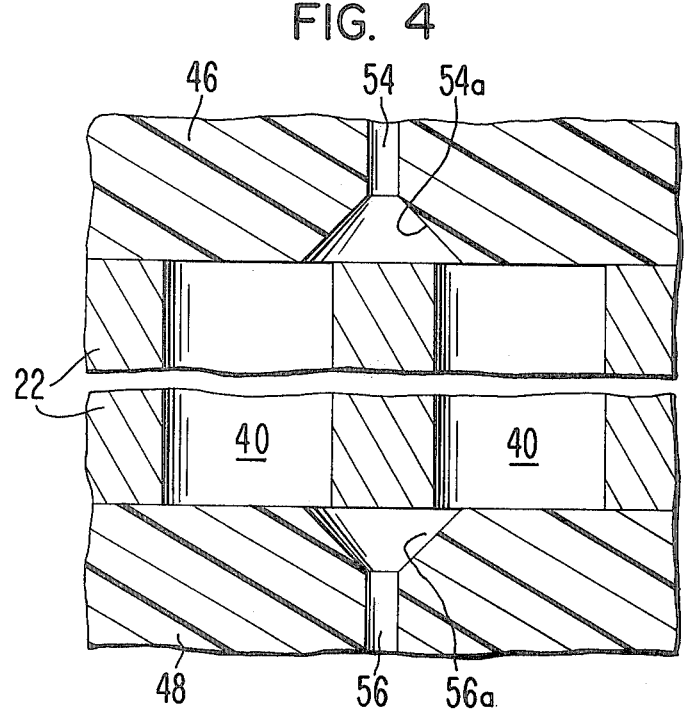
FIG. 4 is a detailed drawing showing the construction of the apertures of the gaskets and their mode of interaction with the inlet and outlet ports of the sample cells.

The elimination of the need to interrupt the flow of carrier fluid as the cylinder 22 is rotated is made possible partly by a particular structural configuration of the apertures 54 and 56 in the gaskets 46 and 48. As seen in FIG. 4, each of the apertures 54 and 56 is provided with a flared portion 54a and 56a, respectively, which flares outwardly in the direction toward the surface of cylinder 22 in each case. The maximum width of each of the flared portions 54a and 56a is greater than the minimum separation between the adjacent inlet ports and the adjacent outlet ports, respectively, of adjacent sample cells 40. Therefore, during some of the time between complete alignment of one sample cell and the next, the apertures 54 and 56 communicate with both of the adjacent sample cells. This structure thus establishes a "make before break" type of communication with succeeding pairs of the sample cells 40. Communication is established with the succeeding sample cell before the communication is completely lost with the sample cell which was previously aligned with the apertures 54 and 56.

This feature assures that at no time is the flow of carrier fluid through this apparatus completely blocked. This is beneficial because it prevents undue buildup of pressure between the pump supplying high pressure carrier fluid and the inlet ports 42 of the sample cells 40. Thus, no pressure buildup occurs across the cylinder 22 other than that due to flow resistance in the individual sample cells 40. If this feature is not provided, the cylinder 22 must be rotated very rapidly between alignment of the several sample cells 40 in order to avoid undesirable and possibly destructive pressure accumulations.

Figure 5:
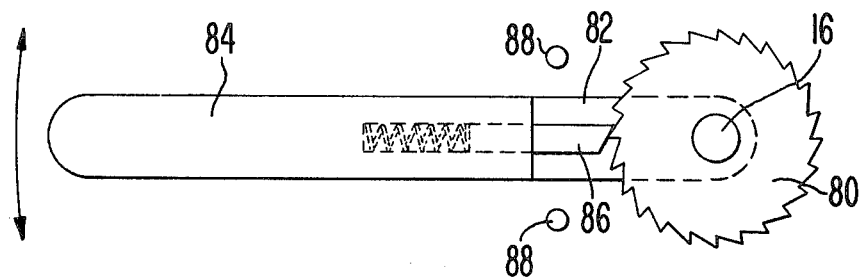
FIG. 5 is a top view illustrating a ratchet mechanism suitable for rotating the sample holding means of this invention.

FIG. 5 illustrates a ratchet wheel 80 mounted on a pivot 82 which is connected to shaft 16. A handle 84 is also mounted on the same pivot. A finger 86, attached to handle 84, engages the teeth of the ratchet wheel 80 when the handle is moved in a clockwise direction as shown in FIG. 5. Pins 88 are provided in order to controlledly limit the degree of motion of handle 84. Pins 88 are spaced so that the motion of handle 84 between its limits of rotation coincides with the angular displacement between the sample cells 40 of cylinder 22. The ratchet mechanism can thus be arranged so that for each motion of the handle, the angular displacement of the cylinder 22 will advance by one sample cell.

Alternate means of effecting rotation of the cylindrical sample holding means 22, including automatic means, are achievable by one of ordinary skill in the art.

Figure 6:
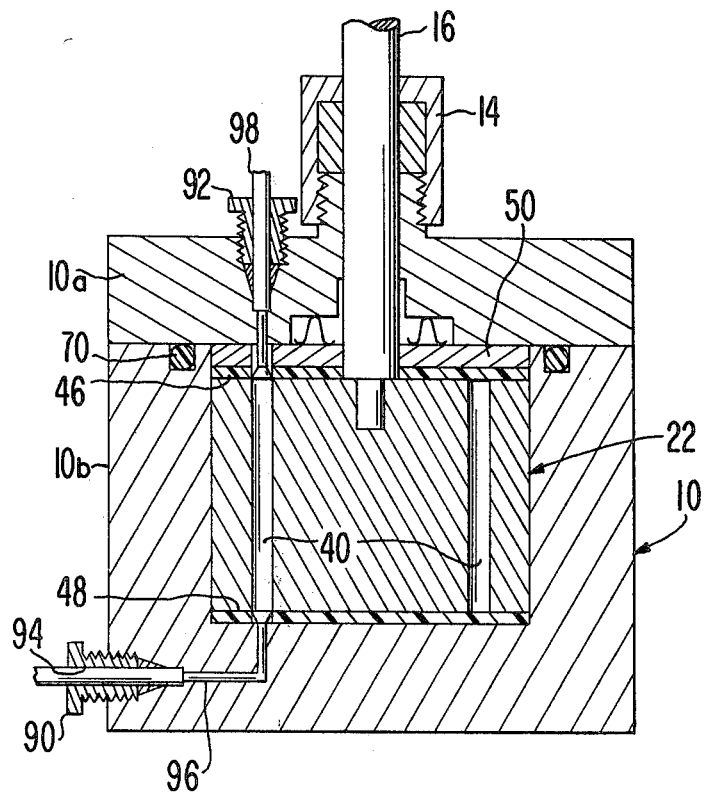
FIG. 6 is a sectional drawing of the apparatus of this invention, showing auxiliary inlet and outlet conduits which may be provided for introduction of samples to the sample cells.

FIG. 6 illustrates optional means for enabling the pre-loading of the sample cells 40 with quantities of the samples to be tested. Plugs 90 and 92 are threadedly engaged in elements 10a and 10b of vessel 10, respectively. The plug 90 has a cylindrical bore 94 therethrough, which forms part of a sample input conduit 96. The other plug 92 has a corresponding bore therethrough forming part of a sample output conduit 98.

Sample input conduit 96 and sample output conduit 98 extend, respectively, to input and output ports which are aligned directly with one another, and are positioned such that any one of the sample cells 40 in cylinder 22 may be aligned therewith by proper rotation of the cylinder. For this purpose, additional apertures must be provided in gaskets 48 and 46 for the sample to pass through into and out of the sample cells 40. The positioning of the conduits 96 and 98 may be such that a sample cell may be filled within one or two increments of motion following its previous expulsion of a sample to the analysis column. In this way, the sample cells may be reloaded with additional samples shortly after having given up the previous sample. This permits continuous operation of the apparatus without interruption of the sample flow, and eliminates the need for stopping the process to reload the sample cells.

It is nonetheless possible to connect the sample input and outlet conduits into the carrier inlet conduit 36. This arrangement would reduce the cost of the apparatus by eliminating a separate sample inlet and outlet conduit, but would necessitate the cessation of testing during loading of the sample cells 40.

This apparatus can be made in a dissemblable fashion by one of normal skill in the art in order to facilitate cleaning and inspection of the interior parts thereof. Similarly, the sample holding cylinder means 22 may be entirely removed from vessel 10 and loaded outside on a jig in a known manner. Ease of dissembly is promoted by the simplicity of this device.

In the sample loading operation, the sample may be introduced at the bottom of the sample cell 40 through the sample inlet conduit 96, filling the sample cell 40. Any excess sample material would exit through sample outlet conduit 98 into a drain or other receptacle. Alternatively, the plug 90 may be replaced with a solid plug, thus sealing sample input conduit 96, and the sample cell 40 may be filled by a syringe needle. This technique is useful where it is desired to meter into the sample cell 40 a predetermined precise amount of sample which is less than the volume of the sample cell. When the filling operation is complete, both of the plugs 92 and 90 may be replaced by solid plugs, rendering the vessel 10 pressure-tight for operation.

It is desirable that the parts of the apparatus of this invention be made of materials which are relatively inert chemically, and which possess substantial physical rigidity. These requirements are fulfilled suitably by making the vessel 10, shaft 16, cylinder 22 and most of the other parts of 316 stainless steel. Gaskets 46 and 48 are suitably composed of TFE "Teflon".

A suitable stainless steel cylindrical sample holding means may be 1⅜ inches in diameter and 3 centimeters long. Such a cylinder may advantageously have twenty-four separate sample cells therein, each sample cell being 0.081 inch in diameter, the centers thereof being spaced evenly around a one-inch diameter circle. In such a configuration the minimum spacing between the cells is 0.05 inch, and each sample cell is capable of holding 100 microliter samples. Appropriate gaskets may be 0.05 inch in thickness.

The invention disclosed herein enables the injection of successive samples into the analysis column without necessitating the interruption of carrier fluid flow, notwithstanding that the injection is accomplished at high pressure. The apparatus can accommodate a large number of samples in a very compact volume. No great machining skill is necessary to manufacture the parts for this apparatus. Unlike prior art high pressure injectors, this injector does not require movable high pressure seals which must be very carefully machined and polished, and which, under the best of circumstances, are not particularly durable.

The transfer of the extreme pressure drops from the movable to the static components further enhances the reliability and durability of the apparatus of this invention. The device is inherently easy to automate because automatic apparatus can easily be provided for rotating the cylinder 22 in order to align successive ones of the sample cells 40 in the carrier fluid stream.

The repeatability of tests performed with this injector is enhanced by the fact that there are no high pressure drops across the sample cylinder 22. In prior art devices, the high pressure drops tended to alter the volume of the sample cells as portions of the sealing mechanisms became extruded into the sample cells themselves.

This apparatus is versatile with respect to sample volume. It is possible to provide a plurality of interchangeable sample holding cylinder means 22 having sample cells of differing size. Additionally, inert filler material may be placed in the sample cells.

The invention of this application, in summary, represents a significant advance in the state of the art of high pressure injectors in liquid chromatography. The disclosure herein is intended to be illustrative of the present invention, and not exhaustive thereof. Persons of ordinary skill in the art will be able to make certain changes, modifications and alterations in the apparatus and method disclosed and claimed herein without departing from the spirit and substance of the invention.

What is claimed is:

1. Apparatus for controlledly injecting each of a plurality of fluid samples into a high pressure environment, said apparatus comprising:
   a. sample holding means comprising a cylinder having a plurality of bores therethrough extending in the axial direction of said cylinder, the axes of said bores being substantially equidistant from the axis of said cylinder, said bores defining a plurality of sample cells for holding the samples,
   b. A pressure-tight vessel defining a chamber for containing said sample holding means, said sample holding means being movably mounted within said chamber,
   c. means for maintaining said chamber at a pressure approximately equal to the pressure of the high pressure environment,
   d. means for moving said sample holding means within said chamber so that each end of each of said bores is selectively connectable to an injection means for forcing the sample out of a bore so connected and into the high pressure environment,
   e. said injection means comprising an inlet conduit connectable to a source of carrier fluid at a pressure at least equal to the pressure of the sample in said chamber, said inlet conduit being selectively connectable to a first end of each of said bores, and said injection means further comprising an outlet conduit extending between said chamber and said high pressure environment, said outlet conduit being selectively connectable to a second end of each of said bores, said inlet and outlet conduits being positioned in said chamber for successive simultaneous connection to said first and second ends of the same one of each of said bores as said sample holding means moves within said chamber,
   f. a first gasket adjacent one end of said cylinder, and a second gasket adjacent the opposite end of said cylinder, each of said first and second gaskets being mounted at the axis of said cylinder for relative movement between said cylinder and said gaskets, each of said first and second gaskets having an aperture, each of said gasket apertures being connected to a different one of said inlet and outlet conduits, the edge of each of said gasket apertures adjacent said cylinder defining a geometrical figure having a transverse dimension which is greater than the minimum spacing between adjacent ones of said bores through said cylinder, and
   g. means for holding each of said first and second gaskets stationary with respect to said vessel.

2. The apparatus of claim 1 wherein:
   a. said sample holding means is rotatably mounted within said chamber by means comprising a shaft extending through a wall of said vessel through a high pressure shaft seal, said shaft being connectable to the center of one end of said cylinder, and
   b. said inlet and outlet conduits extend to corresponding rotational points equidistant from the axis of said cylinder at opposite ends of said cylinder.

3. The apparatus of claim 1, further comprising:
   resilient biasing means connected to at least one of said gaskets for forcing at least said one gasket flush against said cylinder.

4. The apparatus of claim 2 wherein:
   said means for moving said sample holding means comprises a ratchet mechanism connectable to said shaft external to said vessel.

5. The apparatus of claim 4 wherein said ratchet mechanism comprises:
   a. a ratchet wheel having a plurality of ramped depressions concentric to the center of said ramped wheel and arranged in an arcuate pattern thereabout, said ramped wheel being rotationally fixed to said shaft, and
   b. a drive pin mounted for downward engagement with said each of said ramped surfaces, and being movable along said arcuate pattern for engagement with and driving of said ratchet wheel when so engaged.

6. The apparatus of claim 1 wherein:
   said vessel and said sample holding means are made of stainless steel.

7. The apparatus of claim 1 wherein:
   each of said first and second gaskets are composed of tetrafluoroethylene.

8. The apparatus of claim 1 wherein:
   said sample cells are of unequal volumes.

9. The apparatus of claim 1 further comprising:
   particulate packing material located within at least one of said sample cells.

10. The apparatus of claim 1 further comprising:
    a. a sample inlet conduit extending into said vessel from a point external thereof, and being connectable to a source of the fluid sample, and
    b. a sample outlet conduit communicating between the interior and exterior of said vessel, each of said sample inlet and outlet conduits being connectable with corresponding first and second ends of each bore.

11. A method for controlledly injecting each of a plurality of fluid samples into a high pressure environment, said method comprising the steps of:
    a. placing the fluid samples into a sample holding means comprising a plurality of sample cells, each sample cell having an inlet port and an outlet port,
    b. elevating the pressure of the sample holding means to a level substantially equal to the pressure of the high pressure environment,
    c. selectively connecting an outlet conduit between the high pressure environment and the outlet port of each of the sample cells, and establishing communication between the outlet port of the subsequent sample cell to be connected to the high pressure environment prior to interrupting the communication of the high pressure environment with the outlet port of the sample cell previously connected thereto, and
    d. selectively applying pressure to the inlet port of each of said sample cells when the outlet conduit is connected to that sample cell.

12. The method of claim 11 comprising the additional step of:
    maintaining a low pressure seal of each of said sample cells which are not connected to the high pressure environment by way of the outlet conduit.

13. The method of claim 12 in which said step of maintaining said low pressure seal comprises:
    resiliently biasing gaskets against the ports of each of the sample cells which are not connected to said high pressure environment.

14. In a liquid chromatograph for analyzing each of a plurality of fluid samples and having a sample holding means having sample cells for holding the fluid samples, an analysis column maintained at a high pressure, and pressure injection means selectively connectable to each of the sample cells for forcing the fluid sample located in the connected cell into the analysis column, the improvement comprising:

a. a pressure tight vessel enclosing the sample holding means,
b. means for maintaining the pressure of the sample holding means within the pressure tight means at an elevated pressure substantially equal to the pressure of the analysis column,
c. means for maintaining a low pressure seal between the analysis column and those of the sample cells not connected to the analysis column, and
d. means for selectively connecting each of the sample cells to the analysis column, said selectively connecting means comprising means for initiating fluid communication with the successive one of the sample cells to be connected to the analysis column before the cessation of fluid communication between the previous one of the sample cells connected to the analysis column.

* * * * *